US012678595B2

(12) United States Patent
Liu et al.

(10) Patent No.: US 12,678,595 B2
(45) Date of Patent: Jul. 14, 2026

(54) FEEDING DEVICE FOR TUBULAR COMPONENT

(71) Applicant: Precision Robotics (Hong Kong) Limited, Shatin (HK)

(72) Inventors: Ning Liu, Shatin (HK); Sotiris Tsouris, Shatin (HK); Siu Lun Alan Kwok, Shatin (HK)

(73) Assignee: Precision Robotics (Hong Kong) Limited, Shatin (HK)

( * ) Notice: Subject to any disclaimer, the term of this patent is extended or adjusted under 35 U.S.C. 154(b) by 573 days.

(21) Appl. No.: 18/034,594

(22) PCT Filed: Oct. 19, 2021

(86) PCT No.: PCT/CN2021/124689
§ 371 (c)(1),
(2) Date: Apr. 28, 2023

(87) PCT Pub. No.: WO2022/105512
PCT Pub. Date: May 27, 2022

(65) Prior Publication Data
US 2023/0398327 A1      Dec. 14, 2023

(30) Foreign Application Priority Data

Nov. 17, 2020    (HK) ........................... 22020020148.5

(51) Int. Cl.
*A61M 25/01*              (2006.01)
(52) U.S. Cl.
CPC . *A61M 25/0113* (2013.01); *A61M 2205/0205* (2013.01); *A61M 2205/3327* (2013.01)
(58) Field of Classification Search
CPC ........... A61B 1/0016; A61B 2034/301; A61M 2025/018; A61M 2205/0205; A61M 2205/3327; A61M 25/0113
See application file for complete search history.

(56) References Cited

U.S. PATENT DOCUMENTS 6,358,199 B1     3/2002  Pauker et al.
2006/0173239 A1  8/2006  Neumann et al.
(Continued)

FOREIGN PATENT DOCUMENTS

CN        102596306 A      7/2012
CN        104644270 A      5/2015
(Continued)

OTHER PUBLICATIONS

International Search Report for PCT Application No. PCT/CN2021/124689, mailed Jan. 19, 2022.
(Continued)

*Primary Examiner* — Mohamed G Gabr
(74) *Attorney, Agent, or Firm* — Budzyn IP Law, LLC

(57)                ABSTRACT

This patent application relates to a feeding device for tubular component, which includes: a first driver and a first wheel set; and, a second driver and a second wheel set; wherein, the tubular component can be clamped between the first and second wheel sets, and be driven to move under the friction action of the first and second wheel sets; the first wheel set has a plurality of first driving wheels, travelling directions of which are parallel to each other, and form an angle with an extension direction of a clamped portion of the tubular component, the angle being an acute angle; the second wheel set has a plurality of second driving wheels, travelling directions of which are parallel to each other. The technical solution of the present application involves a simple structure, low cost, and ingenious principle, and has applicability to both rigid and flexible tubular components.

15 Claims, 7 Drawing Sheets

(56)                    References Cited

U.S. PATENT DOCUMENTS

| | | | | |
|---|---|---|---|---|
| 2012/0232476 A1* | 9/2012 | Bhat | ............... | A61M 25/09041 |
| | | | | 226/176 |
| 2013/0231678 A1 | 9/2013 | Wenderow et al. | | |
| 2014/0276391 A1 | 9/2014 | Yu | | |
| 2014/0277333 A1* | 9/2014 | Lewis | .................... | A61B 34/30 |
| | | | | 623/1.11 |
| 2014/0316448 A1 | 10/2014 | Higgins | | |
| 2016/0135662 A1* | 5/2016 | Hatakeyama | .......... | A61B 90/96 |
| | | | | 606/130 |
| 2018/0056044 A1 | 3/2018 | Choi et al. | | |
| 2018/0104013 A1 | 4/2018 | Hamamoto et al. | | |

FOREIGN PATENT DOCUMENTS

| | | | |
|---|---|---|---|
| CN | 109561878 | A | 4/2019 |
| CN | 111068164 | A | 4/2020 |
| CN | 111110989 | A | 5/2020 |
| DE | 1020004007935 | A1 | 5/2005 |
| JP | 2017023213 | A | 2/2017 |
| KR | 20180041316 | A | 4/2018 |
| WO | 2016185943 | A1 | 11/2016 |

OTHER PUBLICATIONS

Office Action from Hong Kong Patent Application No. 22020020148.
5, dated Feb. 22, 2023.

* cited by examiner

FEEDING DEVICE FOR TUBULAR COMPONENT

CROSS-REFERENCE TO RELATED APPLICATIONS

This Application is a National Stage Application under 35 U.S.C. § 371 of PCT Application No. PCT/CN2021/124689, filed Oct. 19, 2021, which claims priority to Hong Kong patent Application No. 22020020148.5, filed Nov. 17, 2020, the entire contents of which are incorporated by reference herein.

TECHNICAL FIELD

The present application relates to the technical field of medical devices, and in particular to a feeding device for a tubular component.

BACKGROUND OF THE INVENTION

In many medical procedures, especially minimally invasive surgeries, like endoscopy, cardiac catheterization, and single-port surgery, it is usually necessary to insert a tubular component into the patient body, so that the physician can examine the pathological conditions or manipulate tissues for treatment.

The tubular component entering the human body can be either rigid or flexible. The process of intervening into the human body can be operated with human hands or mechanical apparatus. During operation with human hands, the physician has to hold a proximal handle of the tubular component with one hand, and hold a distal insertion tube of the tubular component with the other hand to feed it into the human body. Such operation is easy to make the physician feel tired, and also makes it difficult for the physician to go away for other activities. Thus, the prior art intervention operation usually requires cooperation of many people to complete tasks such as tissue sampling.

During operation with a mechanical apparatus, the means of pushing or rotating a tubular component from its proximal end, which works well for rigid devices, cannot be applied to flexible devices, because it may easily lead to the buckling or twisting of the flexible hose. Though the prior art further proposes some other solutions, such as imitating the surgeon's hand to feed the tubular component step by step, the complicated mechanism makes it chunky and costly. What is even worse, the resulting intermittent movement is not intuitive for remote manual operation, and could cause trouble for automatic control, thus is not suitable for surgical robots.

SUMMARY OF THE INVENTION

In order to solve or at least partly solve the aforementioned technical problems, the present application provides a feeding device for tubular component, which comprises: a first driver and a first wheel set driven by the first driver; and, a second driver and a second wheel set driven by the second driver; wherein, the tubular component can be clamped between the first wheel set and the second wheel set, and be driven to move under the friction action of the first wheel set and the second wheel set; the first wheel set has a plurality of first driving wheels, travelling directions of which are parallel to each other and form an angle with an extension direction of a clamped portion of the tubular component, the angle being an acute angle; the second wheel set has a plurality of second driving wheels, travelling directions of which are consistent with that of the first wheel set. Preferably, in the above feeding device for tubular component, the first driving wheels in the first wheel set synchronously rotate at the same first speed, and the second driving wheels in the second wheel set synchronously rotate at the same second speed, wherein the first speed is equal to the second speed; an axle direction of the first driving wheels is consistent with an axle direction of the second driving wheels; a rotation direction of the first driving wheels is the same as or opposite to a rotation direction of the second driving wheels.

By configuring the first wheel set and the second wheel set to form the same angle with an extension direction of a clamped portion of the tubular component, and said angle to be an acute angle, the forward movement, backward movement, clockwise rotation and counterclockwise rotation of the tubular component can be simply achieved, so long as rotation directions of the first wheel set and the second wheel set are controlled individually, thereby meeting a need for the medical robot to insert the tubular component into the human body. The technical solution of the application involves a simple structure, low cost, and ingenious principle, and it is applicable to both rigid and flexible tubular components and ensures good reliability.

BRIEF DESCRIPTION OF THE DRAWINGS

In order to better explain embodiments of the present application, relevant drawings will be briefly introduced below. It can be understood that, the drawings described below are only used to illustrate some embodiments of the application, and those of ordinary skill in the art can obtain many other technical features and connection relationships that are not mentioned herein based on these drawings.

REFERENCE SIGNS

1. Housing; 11. Support platform; 12. Movable platform; 13. First bracket; 14. Second bracket; 2. Tubular component; 31. First wheel set; 32. First driver; 321. First driving motor; 322, First transmission mechanism; 3221, Main transmission rod; 3222, Sub transmission rod; 3223, First transmission wheel; 3224, Second transmission wheel; 41, Second wheel set; 42, Second driver; 5. Bacteriostatic membrane; 6, Limit mechanism; 71, Guide bar; 72, Transmission belt; 73, Third driving motor; 8. Sensing module.

DETAILED DESCRIPTION OF EMBODIMENTS

The present application will be described in detail below with reference to the drawings.

The present application provides a feeding device for tubular component. Referring to FIGS. 1 to 12, the feeding device comprises: a first driver 32 and a first wheel set 31 driven by the first driver 32; and, a second driver 42 and a second wheel set 41 driven by the second driver 42. Both the first driver 32 and the second driver 42 may be a motor or a motor set, which may be directly connected to each wheel set, or may be drivingly connected thereto via other structures.

Figure 1:
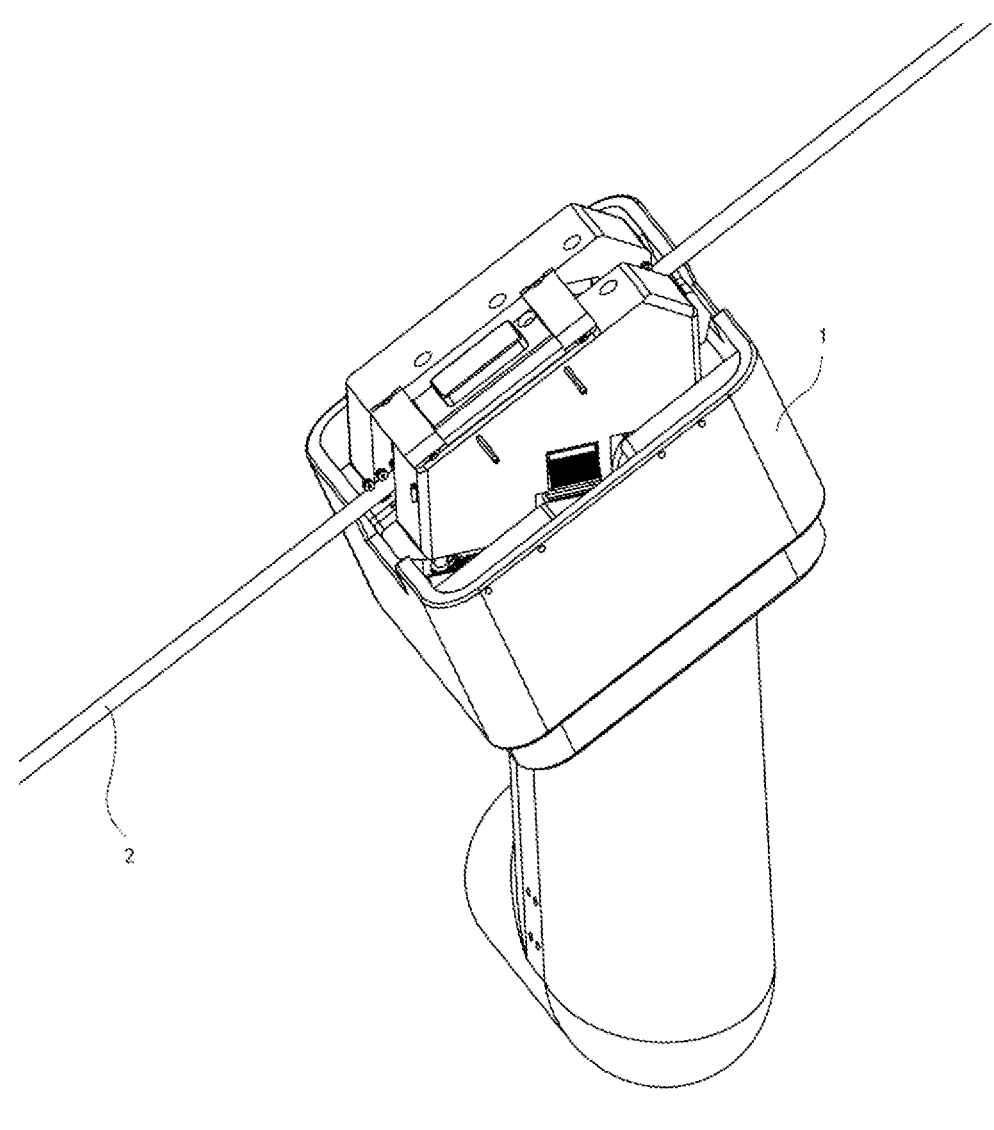
FIG. 1 is a schematic perspective view of a feeding device for tubular component.
Figure 2:
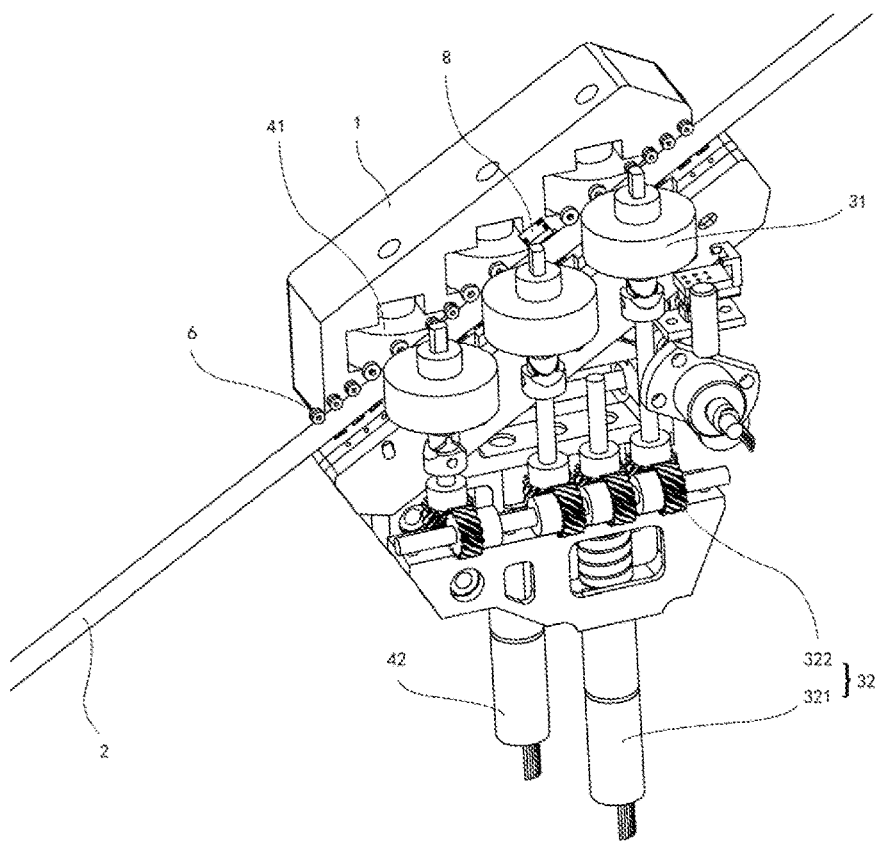
FIG. 2 is a schematic perspective view of an internal structure of the feeding device for tubular component.
Figure 7:
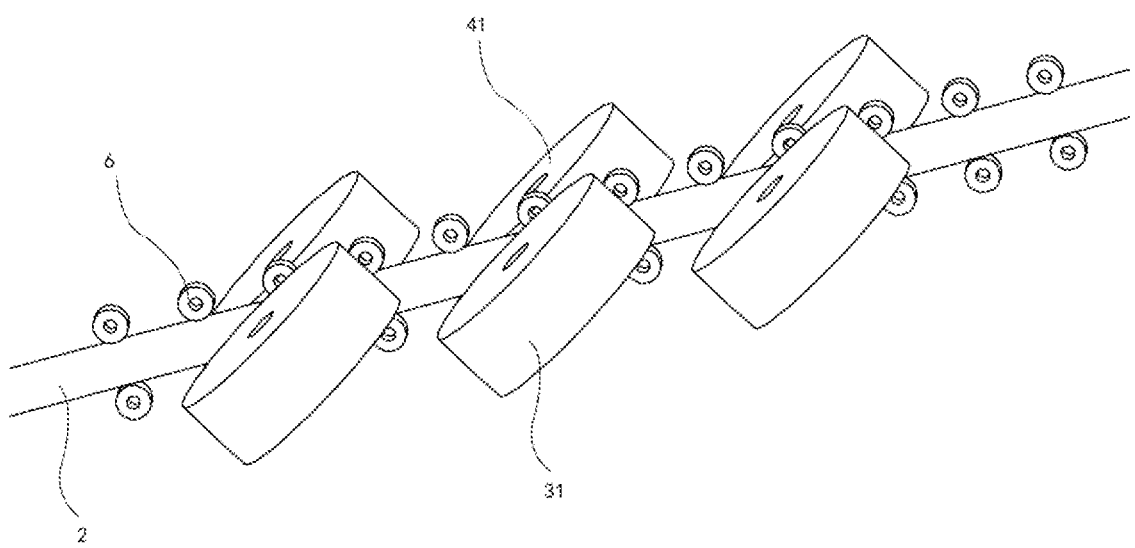
FIG. 7 is a schematic perspective view of the feeding device for tubular component when the wheel set drives the tubular component to move.

Referring to FIGS. 2 and 7, the tubular component 2 can be clamped between the first wheel set 31 and the second wheel set 41, and be driven to move under the friction action of the first wheel set 31 and the second wheel set 41. The first wheel set 31 has a plurality of first driving wheels. The traveling directions of the first driving wheels are parallel to each other, and form an angle with an extension direction of a clamped portion of the tubular component 2, which is an acute angle. The number of the first driving wheels can be at least one, and usually 2 to 6 are preferred. The tubular component can be a rigid tube or a flexible hose. When a rigid tube component is adopted, longitudinal direction of the tubular component is stable, and when a flexible hose is adopted, longitudinal direction of the tubular component would inevitably bend under the influence of its own weight or external force. Accordingly, the application defines "an extension direction of a clamped portion of the tubular component". since the clamped portion of the tubular component tends to maintain a straight shape under the effect of clamping force, its extension direction is a straight line direction collinear with said portion.

Figure 3:
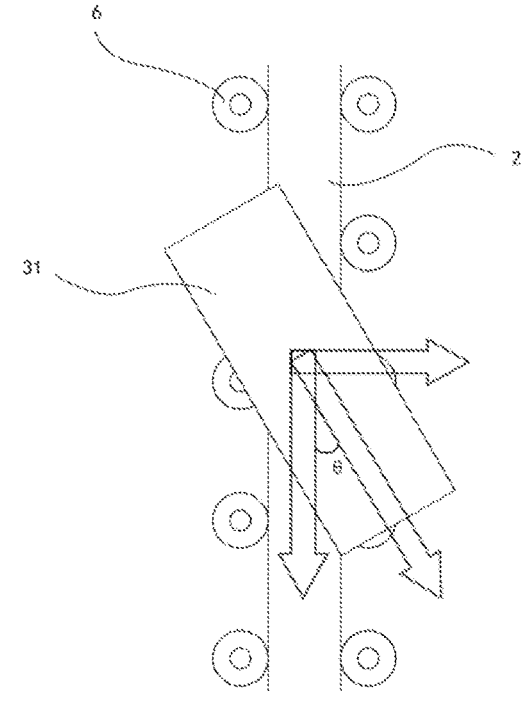
FIG. 3 is a schematic top view of the feeding device for tubular component when the wheel set drives the tubular component to move along its axis.

Referring to FIG. 3, the first driving wheel forms an angle θ with the extension direction of the clamped portion of the tubular component 2. Obviously, when the angle θ is an acute angle, there must be another obtuse angle complementary to said angle θ between the first driving wheel and the tubular component 2. For easy illustration, only the acute angle θ is referred to as the angle between the two in the description. In an embodiment, the angle θ is adjustable.

Figure 4:
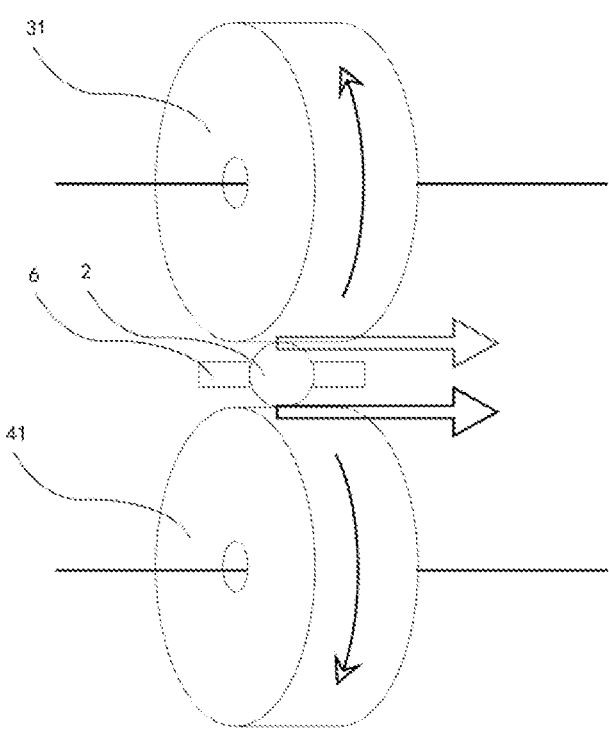
FIG. 4 is a schematic side view of the feeding device for tubular component when the wheel set drives the tubular component to move along its axis.

Referring to FIGS. 2 and 4, the second wheel set 41 has a plurality of second driving wheels, the traveling directions of which are parallel to each other. Preferably, an axle direction of the first driving wheels is consistent with an axle direction of the second driving wheels, such that a rotation direction of the first driving wheels is the same as or opposite to a rotation direction of the second driving wheels. Herein, the "axle direction" refers to an orientation of an axle around which the respective driving wheels rotate, and is orthogonal to the traveling direction of the driving wheels. Accordingly, the movement of the tubular component 2 can be realized, by controlling the movement of the respective driving wheels in the first and second wheel sets 41.

Specifically, when one of the first driving wheels in the first wheel set 31 and the second driving wheels in the second wheel set 41 rotate counterclockwise, and the other rotate clockwise respectively in the arrow direction shown in FIG. 4, the resultant forces acting on the tubular component 2 in its tangential directions would cancel, and the resultant forces acting in its axial direction would be superimposed, so that the tubular component 2 moves along its axis under the cooperative action of the first wheel set 31 and second wheel set 41. The forward and backward movements of the tubular component 2 can be controlled, by varying rotation directions of the respective first driving wheels and second driving wheels.

Figure 5:
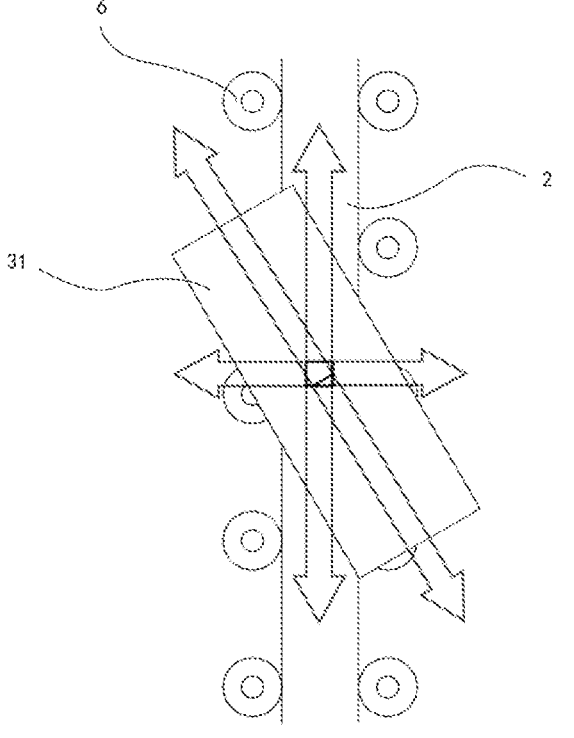
FIG. 5 is a schematic top view of the feeding device for tubular component when the wheel set drives the tubular component to rotate.
Figure 6:
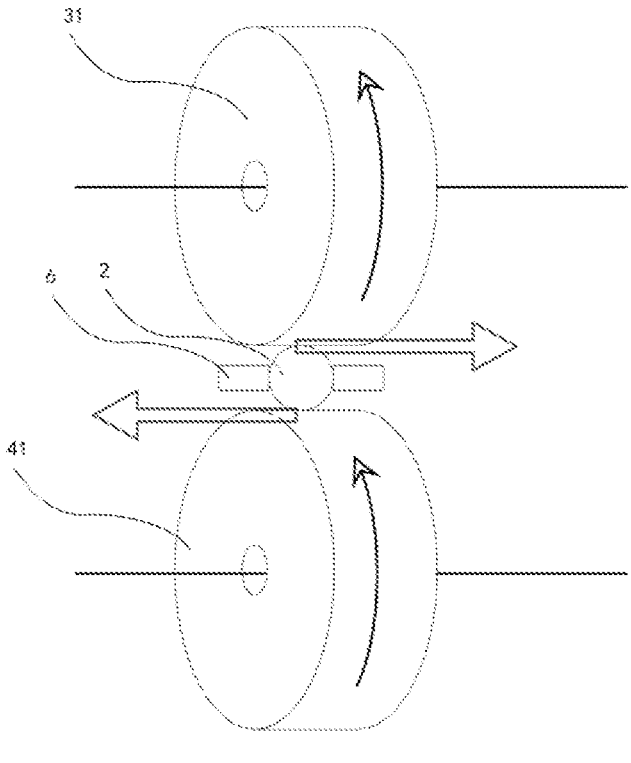
FIG. 6 is a schematic side view of the feeding device for tubular component when the wheel set drives the tubular component to rotate.

Referring to FIGS. 5 and 6, when the first driving wheel in the first wheel set 31 and the second driving wheel in the second wheel set 41 both rotate counterclockwise or clockwise in the arrow direction shown in FIG. 6, the resultant forces acting on the tubular component 2 in its axial direction would cancel, and the resultant forces acting in its tangential directions would be superimposed, so that the tubular component 2 rotates in its circumferential direction under the cooperative action of the first wheel set 31 and second wheel set 41. The rotation directions of the tubular component 2 can be controlled, by varying rotation directions of the respective first driving wheels and second driving wheels.

Obviously, as long as the above-mentioned angle θ is within the range of an acute angle, the movement of the tubular component 2 can be easily controlled. When the angle θ is relatively small, it would be easier for the wheel set to drive the tubular component 2 to move linearly in the axial direction, and when the angle θ is relatively large, it would be easier for the wheel set to drive the tubular component 2 to rotate in its circumferential direction. Therefore, the angle θ can be selected and set according to actual needs. Setting the angle θ in the range of 15° to 75° can make the force acting on the tubular component 2 in both directions more moderate. Since the axial movement of the tubular component 2 is weighted higher when the tubular component 2 is inserted into the human body, the angle θ can be set in the range of 30° to 45°.

In summary, in an embodiment of the present application, the first wheel set 31 and the second wheel set 41 are configured to form the same acute angle with an extension direction of a clamped portion of the tubular component 2. Thus, the forward movement, backward movement, clockwise rotation and counterclockwise rotation of the tubular component 2 can be simply realized, so long as rotation directions of the first wheel set 31 and the second wheel set 41 are controlled individually, thereby satisfying the need for the medical robot to insert the tubular component 2 into the human body. The technical solution of the present application involves a simple structure, low cost, and ingenious principle, and it is applicable to both rigid and flexible tubular components and ensures good reliability.

Further, the feeding device for tubular component may also comprise a limit mechanism 6, which is arranged in pairs on both sides of the tubular component 2 so as to restrict the tubular component 2 between the first wheel set 31 and the second wheel set 41. The limit mechanism 6 can prevent the tubular component 2 from getting rid of clamping from the first wheel set 31 and the second wheel set 41, and improve the stability of its movement.

The limit mechanism 6 may be implemented with a plurality of means. For instance, the limit mechanism 6 may comprise several pairs of guide wheels arranged at intervals in the extension direction of the clamped portion of the tubular component 2, as shown in FIGS. 2 and 7. Also, the limit mechanism 6 may comprise several pairs of rolling balls protruding toward the clamped portion of the tubular component 2, or several pairs of smooth faces protruding toward the clamped portion of the tubular component 2. Among them, the configuration of rolling balls has uniform friction in all directions, and can well support the axial and rotational movements of the tubular component 2. Where the foregoing limit mechanism 6 is applied, the friction between the tubular component 2 and the limit mechanism 6 could be minimized, so as to facilitate the movement of the tubular component 2.

Many of the aforementioned members in the feeding device may be installed in a housing 1 or a bracket to provide the relatively fixed positions. Referring to FIG. 2, the feeding device for tubular component may include a housing 1. Further referring to FIG. 11, the housing 1 may comprise: a support platform 11, which is arranged between the first wheel set 31 and the second wheel set 41, the limit mechanism 6 at one side being located on the support platform 11; and a movable platform 12, on which the limit mechanism 6 at the other side is located. The movable platform 12 can move relative to the support platform 11 to a location opposite to the support platform 11, so that the limit mechanism 6 restricts the tubular component 2 between the first wheel set 31 and the second wheel set 41. Relative movement of the movable platform 12 can be realized through a rotating shaft or a sliding rail. Cooperation of the support platform 11 and the movable platform 12 can facilitate the placement and removal of the tubular component 2.

The feeding device for tubular component may further comprise: a first bracket 13 in which the first wheel set 31 is disposed; and a second bracket 14 in which the second wheel set 41 is disposed. Both the first bracket 13 and the second bracket 14 may be a part of the housing 1. In addition, the feeding device for tubular component may further include a guide bar 71. The first bracket 13 and the second bracket 14 are both arranged on the guide bar 71. The second bracket 14 can move in a direction toward or away from the the first wheel set 31 along the guide bar 71, so as to clamp the tubular component 2 between the first wheel set 31 and the second wheel set 41.

There are many available arrangements for the guide bar 71. For example, the guide bar 71 may be a sliding rail. The first bracket 13 is fixed on the slide rail, and the second bracket 14 is slidable on the slide rail. A lock may be provided on the second bracket 14 to fix the relative positions of the second bracket 14 on the guide bar 71. Further, a spring may be provided on the guide bar 71, so that the second bracket 14 tends to move in a direction toward the first bracket 13 under the action of spring. Through the adjustment or replacement of the spring, the pressure of the first wheel set 31 and the second wheel set 41 on the tubular component 2 can be adjusted.

Figure 11:
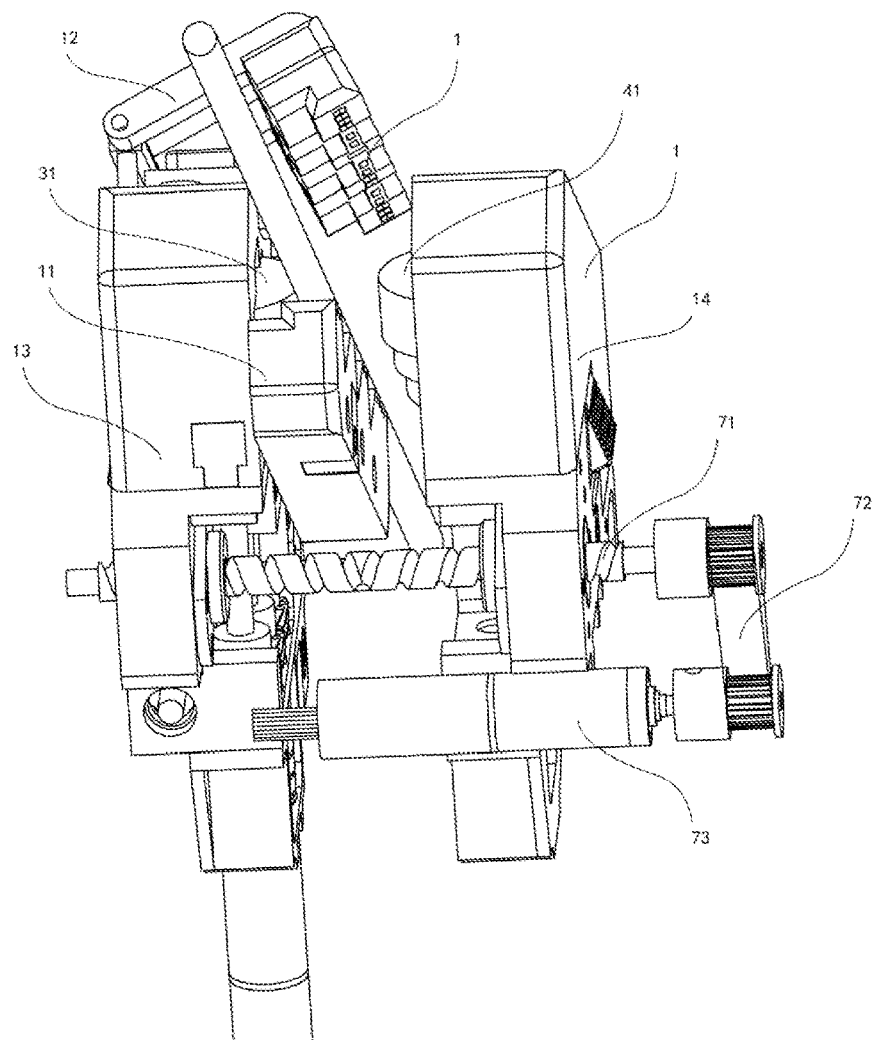
FIG. 11 is a schematic perspective view of a limit mechanism and a guide bar of the feeding device for tubular component.
Figure 12:
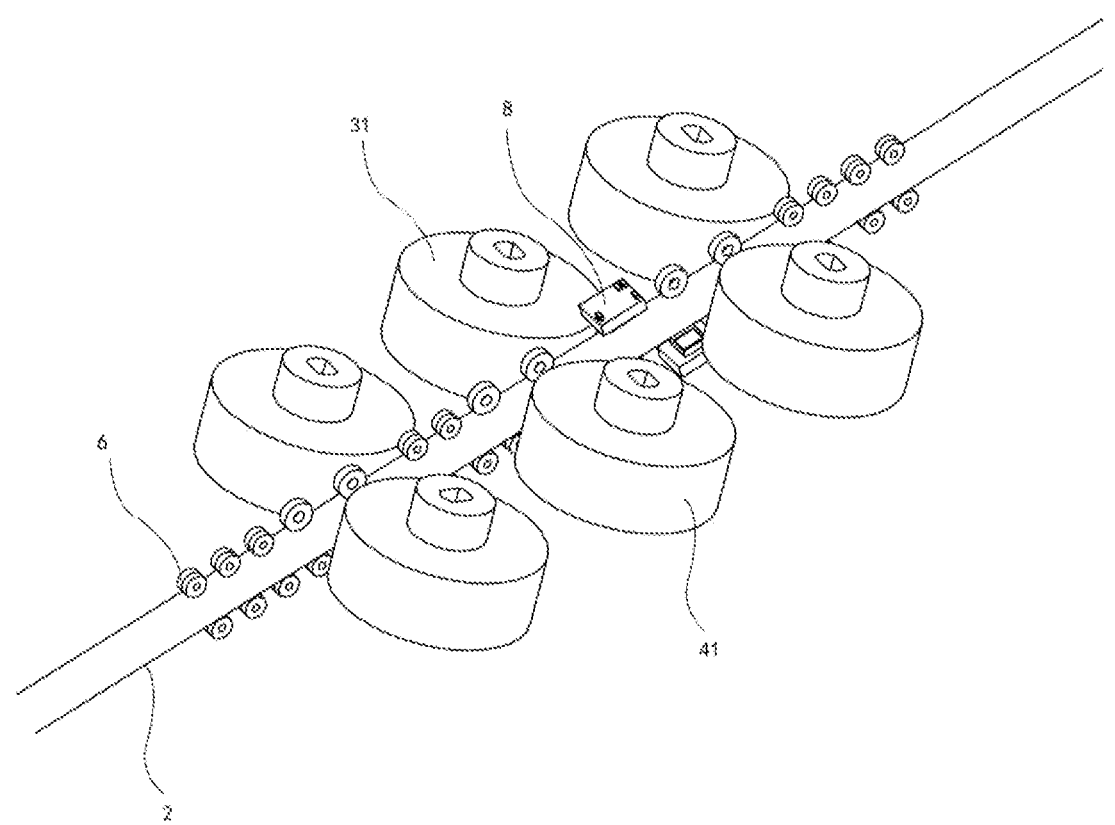
FIG. 12 is a schematic view of the arrangement of a sensing module of the feeding device for tubular component.

Referring to FIG. 11, the guide bar 71 may be a lead screw. In this case, the feeding device may include a third driving motor 73 and a transmission belt 72. The guide bar 71 is connected with the third driving motor 73 via the transmission belt 72. The third driving motor 73 drives the guide bar 71 to rotate via the transmission belt 72, so that the second bracket 14 moves in a direction toward or away from the first bracket 13 along the guide bar 71. When the third driving motor 73 is configured to drive the second bracket 14 to move, movement of the second bracket 14 can be automatically controlled without the need for manual operation. The lead screw itself can prevent uncontrolled sliding of the second bracket 14. By controlling rotation parameters of the third driving motor 73, it is possible to memorize the positions of the second bracket 14 where the optimum pressure(s) is provided to the tubular components 2 with various diameters, which is extremely convenient.

In actual use, the tubular component 2 can be placed onto the support platform 11, and the second bracket 14 can be moved along the guide bar 71 to a location where the first wheel set 31 and the second wheel set 41 apply an appropriate pressure to the tubular component 2. Then, the movable platform 12 is moved to a location opposite to the support platform 11, restricting the location of the tubular component 2. Compared with the feeding device for tubular component in the prior art, the feeding device provided in the present application can adjust the pressure of the first wheel set 31 and the second wheel set 41 on the tubular component 2 at any time as needed, and it is also possible to put in or take out the tubular component 2 at any time as needed, which is extremely convenient.

Each of the wheel sets may comprise a plurality of driving wheels. Referring to FIGS. 2 and 7, these driving wheels can be arranged at appropriate intervals so as to better prevent the tubular component 2 from bending. Optionally, the first driving wheels are arranged at equal intervals in the extension direction of the clamped portion of the tubular component 2, which can improve driving stability of the wheel set. The arrangement of the second wheel set 41 may be consistent with that of the first wheel set 31. Hereinafter, the limitation on the first wheel set 31 can also be applied to the second wheel set 41, unless otherwise explained, so the specific structure of the second wheel set 41 will not be additionally described.

The numbers of the first driving wheel and the second driving wheel may be the same or different. When the numbers are different, additional calculation, adjustment and configuration of rotational speed of the two sets of driving wheels are needed to ensure that reverse resultant forces acting on the tubular component 2 can still cancel when they rotate in the same direction, which would lead to an increased complexity of the system. In this application, the first driving wheels and the second driving wheels are equal in the number, and are arranged in one-to-one correspondence. The respective first driving wheels in the first wheel set 31 rotate synchronously at the same first speed, and the respective second driving wheels in the second wheel set 41 synchronously rotate at the same second speed, wherein the first speed is equal to the first speed. A rotation direction of the first driving wheel is the same as or opposite to a rotation direction of the second driving wheel. Such configuration can not only reduce the complexity of the system, but also ensure that the forces acting on the tubular component 2 in two directions are balanced, thereby preventing it from being twisted, and improving the reliability of the system.

Figure 8:
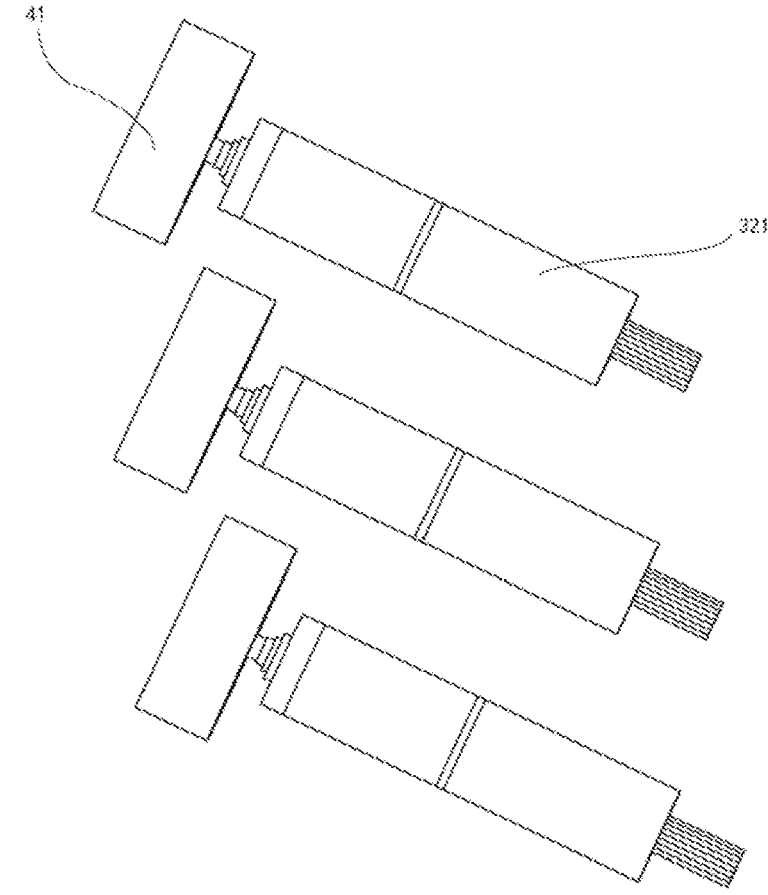
FIG. 8 is a schematic view of the feeding device for tubular component when the motor is directly connected to each driving wheel.

FIG. 8 shows a design in which the wheel set is directly connected to a shaft of the motor. This design has a simple structure. However, the outputs of different motors may be different, and adjustments in advance may be necessary. After a period of use, such difference may be even enlarged, resulting in more cumbersome maintenance. To avoid this defect, the first driver 32 may include a first driving motor 321 and a first transmission mechanism 322 connected to the first driving motor 321. Each first driving wheel is drivingly connected to the first driving motor 321 via the first transmission mechanism 322, so as to be driven by the first driving motor 321. Therefore, with the first transmission mechanism 322, the output of one single motor can act on different driving wheels, which improves consistency of the driving wheels.

Figure 9:
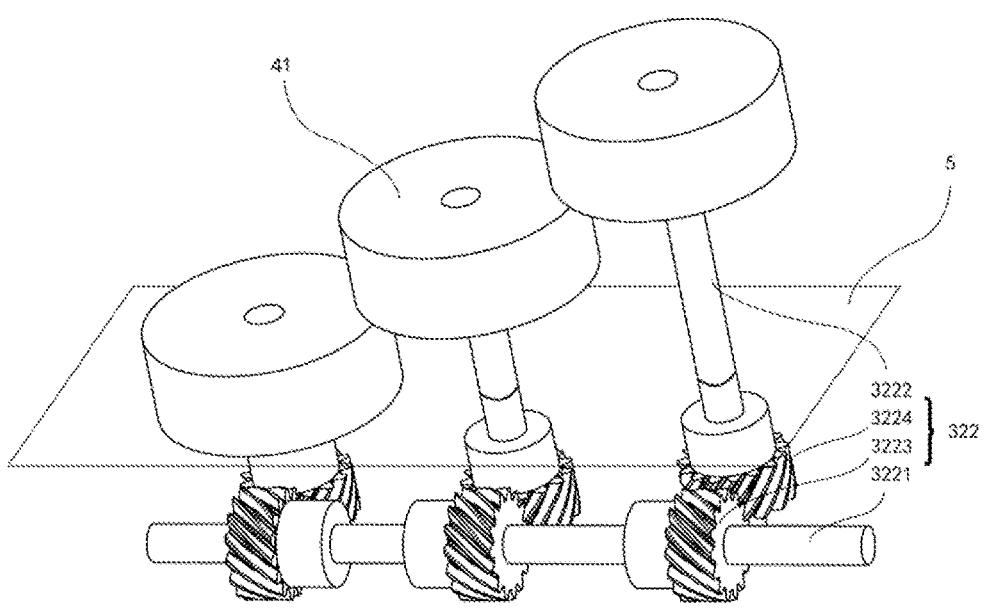
FIG. 9 is a schematic view of a first transmission mechanism of the feeding device for tubular component when helical gears are used for transmission.
Figure 10:
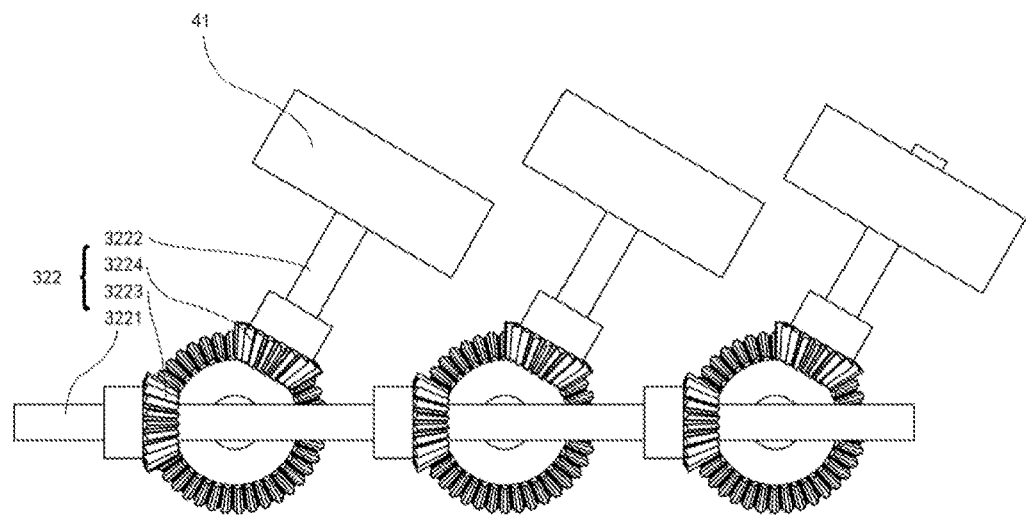
FIG. 10 is a schematic view of a first transmission mechanism of the feeding device for tubular component when bevel gears are used for transmission.

Referring to FIGS. 9 and 10, the first transmission mechanism 322 may include: a main transmission rod 3221 connected with the first driving motor 321, a plurality of first transmission wheels 3223 being mounted to the main transmission rod 3221; and, a plurality of sub transmission rods 3222 coaxially connected with each of the first driving wheels respectively, a second driving wheel 3224 being mounted to the sub transmission rods 3222. The first transmission wheel 3223 is drivingly connected to the second transmission wheel 3224 in one-to-one correspondence. In the embodiment shown in FIG. 8, the first transmission wheel 3223 and the second transmission wheel 3224 are both helical gears, and are directly meshed with each other. In this case, only two helical gears are needed to realize the linkage between the main transmission rod 3221 and the sub transmission rod 3222, and to convert the transmission direction of the force. This design has a very simple structure and very high stability even with a small space occupation. In the embodiment shown in FIG. 9, the first transmission wheel 3223 and the second transmission wheel 3224 are both bevel gears, and are meshed with another bevel gear perpendicular to the two. When the bevel gears instead of helical gears are adopted, the loss of gears is smaller, and thus the service life is longer. In addition, as for the first transmission mechanism 322 provided with a sub transmission rod 3222, the sub transmission rod 3222 may further include a first part and a second part detachably connected with each other, wherein the first part is connected with the second transmission wheel 3224, and the second part is connected with the first driving wheel.

Of course, the first transmission mechanism 322 may be arranged in many other ways. For instance, the first transmission mechanism 322 may include a train wheel structure connected by a transmission rod, and each train wheel varies the transmission direction by a bevel gear to drive each driving wheel to move. The first transmission mechanism 322 may adopt a combination of a spur gear and a bevel gear to convert the transmission direction of the force.

Referring to FIG. 9, the feeding device may further comprise a bacteriostatic membrane 5 located between the first part and the second part, wherein the second part passes through the bacteriostatic membrane 5 to be detachably connected with the first part. Thereby, once the feeding device for tubular component has already been used for one patient, such mechanisms as the bacteriostatic membrane 5, the tubular component 2 along with the second part of the sub transmission rod 3222 and each driving wheel can be discarded, leaving the uncontaminated and high-value components such as the drivers and the main transmission rod 3221. Therefore, it is ensured that disposable parts are thrown upon use and more sanitary conditions are met, while the using costs of the feeding device is also reduced.

In addition, referring to FIGS. 2, 3, 5 and 7, the feeding device for tubular component may further include a sensing module 8, which is arranged next to the tubular component 2 and can send the monitored motion state information (e.g. the insertion depth, rotation angles, and the corresponding translation velocity or rotation velocity, etc.) of the clamped portion of the tubular component 2 to an external host computer. The host computer can be a computer that controls a medical robot. Generally, respective mechanisms of the medical robot can be controlled by the host computer, so that these mechanisms can cooperate with each other. In this application, with the motion state information provided by the sensing module 8, the host computer can obtain the current feeding depth and angle of the tubular component 2, making it more convenient for physician to operate.

The sensing module 8 may include a plurality of sensors disposed at different positions around the tubular component 2. Specifically, the sensing module 8 may adopt an optical sensor, such as a laser surface velocity meter, a grating ruler displacement sensor, and so on. The optical sensor can measure movement and rotation speeds and travel distance of the tubular component 2 in a non-contact manner, so that abundant motion state information can be obtained without affecting the movement of the tubular component 2.

Further, a processing module may be provided in the feeding device for tubular component, and the processing module is in communication with the sensing module 8, the first driver 32 and the second driver 42, respectively. The sensing module 8 can send the monitored motion state information of the clamped portion of the tubular component 2 to the processing module, and the processing module can generate a drive compensation signal according to the motion state information and send it to the first driver 32 and/or the second driver 42. The processing module can receive the motion state information and provide a signal feedback to the first driver 32 or the second driver 42 in time. The signal feedback plays an important role. For instance, in a scenario where the tubular component 2 is only required to advance along the axial direction, if the rotation speeds of the first wheel set 31 and the second wheel set 41 are not well matched, the tubular component 2 may be caused to rotate while advancing, which would lead to distortion. On some occasions, the applied frictions on the clamped tubular component from the first wheel set 31 and the second the wheel set 41 may not be the same, which could result from the skidding of certain wheels or the different rotating speeds of these two wheel sets. Thereby, the clamped tubular component 2 will not undergo pure translation or rotation but a mixed helical movement. In order to avoid this, the drive compensation signal generated by the processing module can adjust the output of each driver in time, correct and avoid occurrence of distortion, and ensure the continuity and stability of the feeding process.

While the present application has been described in detail with reference to only a limited number of embodiments, it shall be understood that the present application is not limited to such disclosed embodiments. Rather, the present application can be modified to incorporate any number of variations, alterations, substitutions or equivalent arrangements which are heretofore not described, but are commensurate with the spirit and scope of the application. Additionally, while various embodiments of the present application have been described, it shall be understood that each aspect of the present application may include only some of the described embodiments. Therefore, the present application is not limited by the foregoing description, but is only limited by the scope of the appended claims.

What is claimed is:

1. A feeding device for tubular component, comprising:
a first driver (32) and a first wheel set (31) driven by the first driver (32), wherein the first driver (32) comprises a first driving motor (321) and a first transmission mechanism (322) coupled to the first driving motor (321); and
a second driver (42) and a second wheel set (41) driven by the second driver (42);
wherein, the tubular component (2) can be clamped between the first wheel set (31) and the second wheel set (41), and be driven to move under the friction action of the first wheel set (31) and the second wheel set (41);

the first wheel set (31) has a plurality of first driving wheels, travelling directions of which are parallel to each other, and form an angle with an extension direction of a clamped portion of the tubular component (2), the angle being an acute angle, wherein, each of the first driving wheels is drivingly connected with the first driving motor (321) via the first transmission mechanism (322), so as to be driven by the first driving motor (321);

the second wheel set (41) has a plurality of second driving wheels, travelling directions of which are parallel to each other;

the first driving wheels in the first wheel set (31) synchronously rotate at the same first speed, and the second driving wheels in the second wheel set (41) synchronously rotate at the same second speed, wherein the first speed is equal to the second speed;

an axle direction of the first driving wheels is consistent with an axle direction of the second driving wheels;

a rotation direction of the first driving wheels is the same as or opposite to a rotation direction of the second driving wheels; and wherein the first transmission mechanism (322) comprises:

a main transmission rod (3221) connected with the first driving motor (321), a plurality of first transmission wheels (3223) being mounted to the main transmission rod (3221); and a plurality of sub transmission rods (3222) coaxially connected with each of the first driving wheels respectively, a second wheel (3224) being mounted to the sub transmission rod (3222), wherein, the first transmission wheel (3223) is drivingly connected to the second transmission wheel (3224) in one-to-one correspondence.

2. The feeding device for tubular component according to claim 1, wherein the angle is in a range of 15° to 75°.

3. The feeding device for tubular component according to claim 1, wherein the first driving wheels are arranged at equal intervals in the extension direction of the clamped portion of the tubular component (2).

4. The feeding device for tubular component according to claim 1, wherein the first driving wheels and the second driving wheels are equal in the number.

5. The feeding device for tubular component according to claim 1, wherein:

the first transmission wheel (3223) and the second transmission wheel (3224) are both bevel gears, and are meshed with another bevel gear perpendicular to them; or, the first transmission wheel (3223) and the second transmission wheel (3224) are both helical gears, and are directly meshed with each other.

6. The feeding device for tubular component according to claim 1, wherein, the sub transmission rod (3222) comprises a first part and a second part detachably connected with each other, wherein the first part is connected with the second transmission wheel (3224), and the second part is connected with the first driving wheels;

the feeding device further comprises a bacteriostatic membrane (5) located between the first part and the second part, and the second part passes through the bacteriostatic membrane (5) to detachably connect with the first part.

7. The feeding device for tubular component according to claim 1, further comprising a limit mechanism (6), which is arranged in pairs on both sides of the tubular component (2) so as to restrict the tubular component (2) between the first wheel set (31) and the second wheel set (41).

8. The feeding device for tubular component according to claim 7, wherein the limit mechanism (6) comprises:

several pairs of guide wheels arranged at intervals in the extension direction of the clamped portion of the tubular component (2); or, several pairs of rolling balls protruding toward the clamped portion of the tubular component (2); or, several pairs of smooth faces protruding toward the clamped portion of the tubular component (2).

9. The feeding device for tubular component according to claim 7, further comprising a housing (1), which comprises:

a support platform (11) arranged between the first wheel set (31) and the second wheel set (41), the limit mechanism (6) at one side being located on the support platform (11); and a movable platform (12) on which the limit mechanism (6) at the other side is located, the movable platform (12) being movable relative to the support platform (11) to a location opposite to the support platform (11), so as to restrict the tubular component (2) between the first wheel set (31) and the second wheel set (41) with the limit mechanism (6).

10. The feeding device for tubular component according to claim 1, further comprising:

a first bracket (13) in which the first wheel set (31) is disposed;

a second bracket (14) in which the second wheel set (41) is disposed; and, a guide bar (71) on which the first bracket (13) and the second bracket (14) are both arranged, the second bracket (14) being movable in a direction toward or away from the first bracket (13) along the guide bar (71), so as to clamp the tubular component (2) between the first wheel set (31) and the second wheel set (41).

11. The feeding device for tubular component according to claim 10, further comprising a third driving motor (73) and a transmission belt (72), wherein, the guide bar (71) is a lead screw connected with the third driving motor (73) via the transmission belt (72);

the third driving motor (73) drives the guide bar (71) to rotate via the transmission belt (72), so that the second bracket (14) is movable in a direction toward or away from the first bracket (13) along the guide bar (71).

12. The feeding device for tubular component according to claim 1, further comprising a sensing module (8), which is arranged next to the tubular component (2), and sends monitored motion state information of the clamped portion of the tubular component (2) to an external host computer.

13. The feeding device for tubular component according to claim 12, wherein the monitored motion state information includes insertion depth, rotation angles, translation velocity or rotation velocity.

14. The feeding device for tubular component according to claim 12, further comprising a processing module, which is in communication with the sensing module (8), the first driver (32) and the second driver (42), respectively;

wherein, the sensing module (8) sends the monitored motion state information of the clamped portion of the tubular component (2) to the processing module;

the processing module generates a drive compensation signal according to the motion state information, and sends it to the first driver (32) and/or the second driver (42), to avoid the helical movement or distortion of the tubular component (2).

15. A feeding device for tubular component, comprising:

a first driver (32) and a first wheel set (31) driven by the first driver (32);

a second driver (42) and a second wheel set (41) driven by the second driver (42);

a first bracket (13) in which the first wheel set (31) is disposed;

a second bracket (14) in which the second wheel set (41) is disposed;

a third driving motor (73);

a transmission belt (72); and, a guide bar (71) on which the first bracket (13) and the second bracket (14) are both arranged, the second bracket (14) being movable in a direction toward or away from the first bracket (13) along the guide bar (71), so as to clamp the tubular component (2) between the first wheel set (31) and the second wheel set (41), wherein, the tubular component (2) can be clamped between the first wheel set (31) and the second wheel set (41), and be driven to move under the friction action of the first wheel set (31) and the second wheel set (41);

the first wheel set (31) has a plurality of first driving wheels, travelling directions of which are parallel to each other, and form an angle with an extension direction of a clamped portion of the tubular component (2), the angle being an acute angle;

the second wheel set (41) has a plurality of second driving wheels, travelling directions of which are parallel to each other;

the guide bar (71) is a lead screw connected with the third driving motor (73) via the transmission belt (72); and, the third driving motor (73) drives the guide bar (71) to rotate via the transmission belt (72), so that the second bracket (14) is movable in a direction toward or away from the first bracket (13) along the guide bar (71).

* * * * *